United States Patent
Wilson

(10) Patent No.: US 10,062,274 B2
(45) Date of Patent: *Aug. 28, 2018

(54) RECOGNIZING ALARM FATIGUE IN A CLINICAL SETTING

(71) Applicant: GLOBESTAR SYSTEMS, Toronto (CA)

(72) Inventor: Jason Wilson, Toronto (CA)

(73) Assignee: Globestar, Inc., Toronto (CA)

( * ) Notice: Subject to any disclaimer, the term of this patent is extended or adjusted under 35 U.S.C. 154(b) by 27 days.

This patent is subject to a terminal disclaimer.

(21) Appl. No.: 15/291,645

(22) Filed: Oct. 12, 2016

(65) Prior Publication Data

US 2018/0102047 A1    Apr. 12, 2018

(51) Int. Cl.
| | |
|---|---|
| G08B 1/00 | (2006.01) |
| G08B 29/18 | (2006.01) |
| A61B 5/00 | (2006.01) |
| G08B 29/02 | (2006.01) |

(52) U.S. Cl.
CPC ............ *G08B 29/185* (2013.01); *A61B 5/746* (2013.01); *G08B 29/02* (2013.01)

(58) Field of Classification Search
CPC ........ G08B 29/185; G08B 29/02; A61B 5/746
USPC ............................ 340/506, 539.1, 3.1, 573.1
See application file for complete search history.

(56) References Cited

U.S. PATENT DOCUMENTS

| | | | |
|---|---|---|---|
| 9,098,604 B2 | 8/2015 | Treacy | |
| 2014/0005502 A1* | 1/2014 | Klap | A61B 5/0205 600/301 |
| 2015/0164438 A1* | 6/2015 | Halperin | A61B 5/746 340/573.1 |
| 2016/0090097 A1* | 3/2016 | Grube | B60W 40/08 340/576 |

\* cited by examiner

*Primary Examiner* — Daryl Pope
(74) *Attorney, Agent, or Firm* — Robert Schuler

(57) ABSTRACT

A notification system operating in a healthcare setting maintains information in alarm messages received from each of a plurality of call points and in messages received from clinicians, and operates on this information to determine whether a clinician is currently suffering from alarm fatigue or is at risk of suffering from alarm fatigue at some future time.

19 Claims, 8 Drawing Sheets

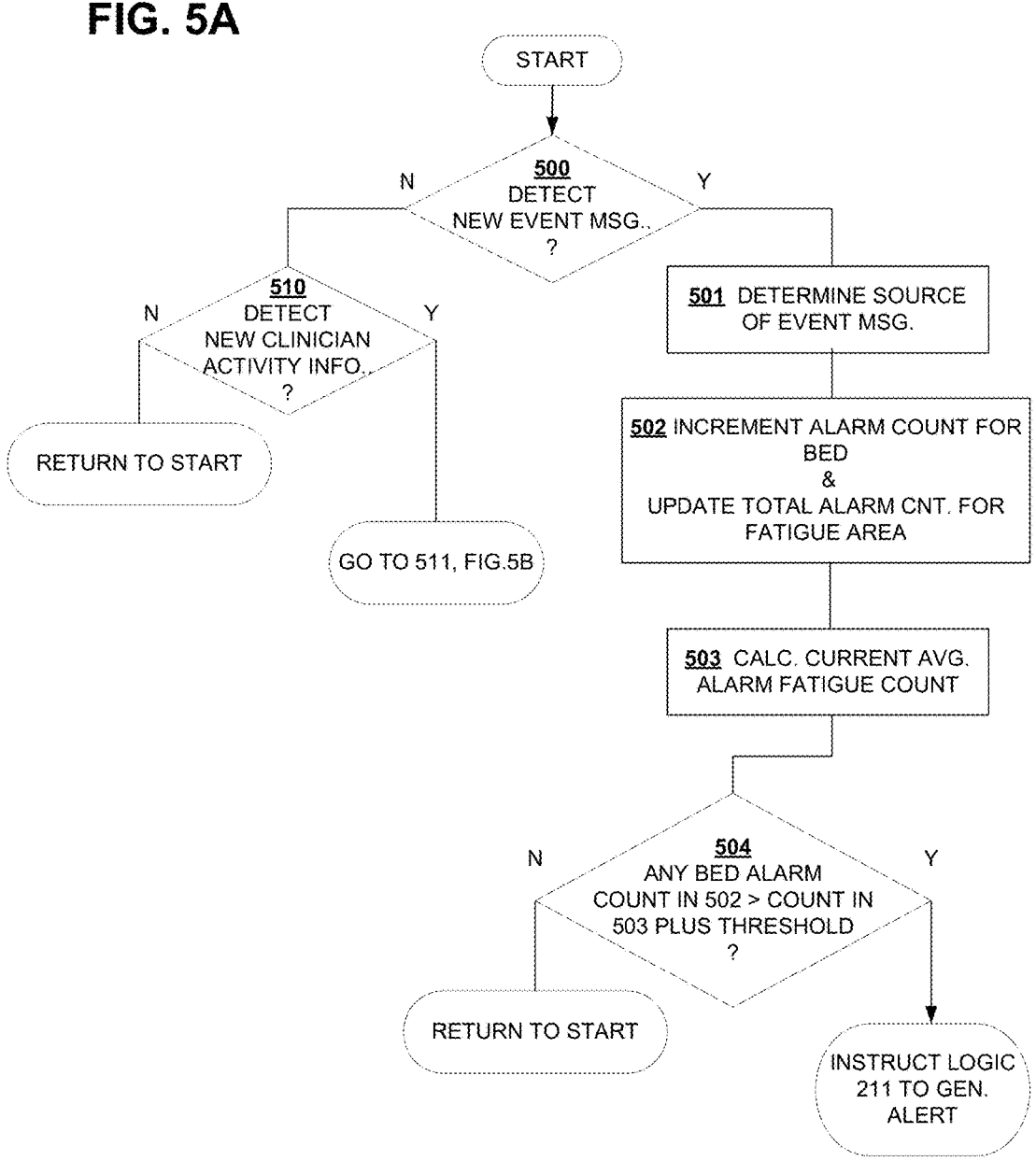

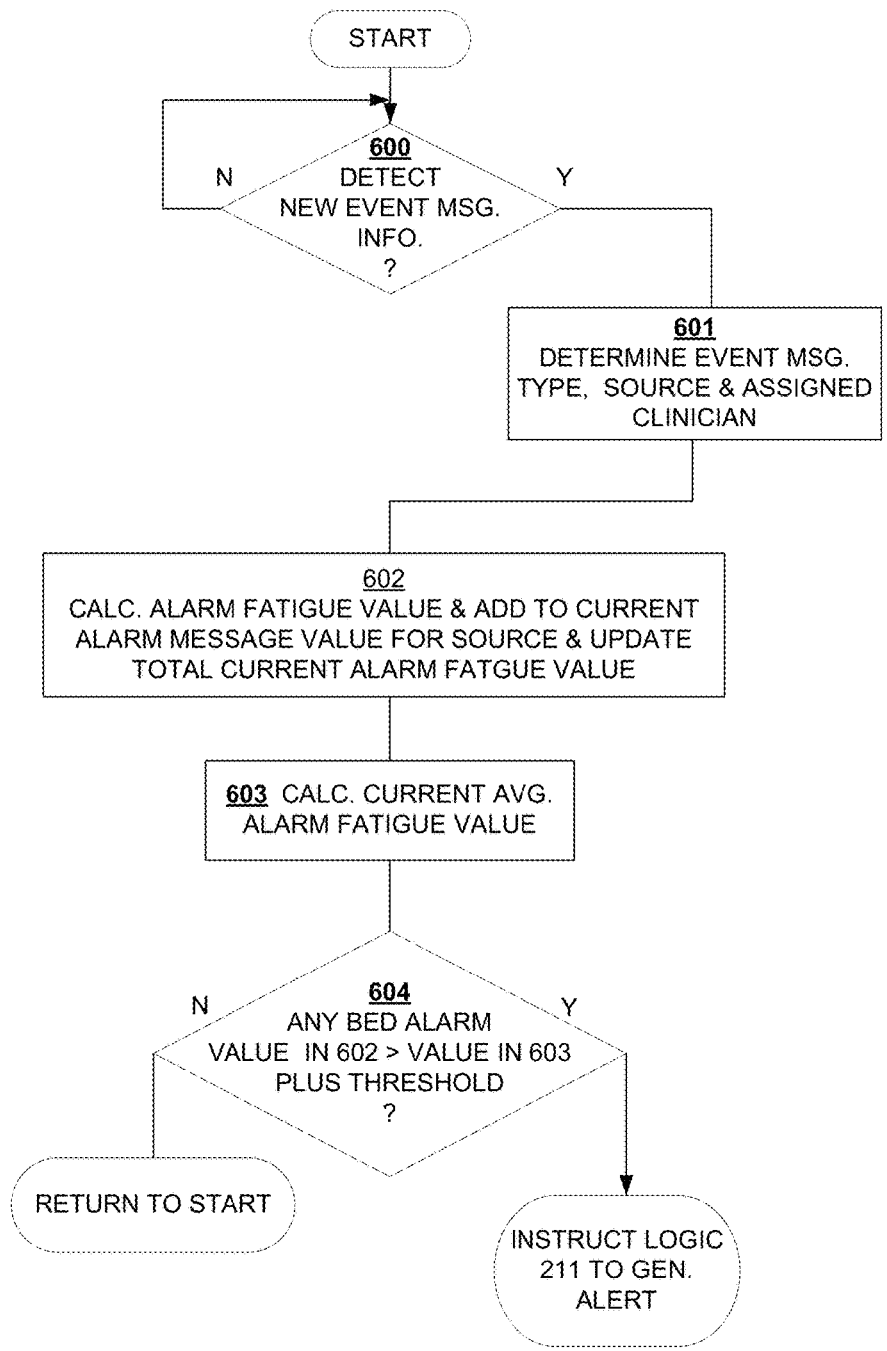

RECOGNIZING ALARM FATIGUE IN A CLINICAL SETTING

BACKGROUND

1. Field of the Invention

The present disclosure relates to a process for identifying the occurrence of alarm fatigue in a clinical setting, and generating and sending an alert message in response.

2. Background

Healthcare organizations place a high value on receiving and responding, in real-time or near real-time, to patient or non-patient related events. These events can be generated by any number of different devices that can be connected to a healthcare communication network, such as patient monitors, patient call devices, nurse call devices, operating room communication devices to name only a few. For example, an event can be generated as the result of the collection by a patient monitor of real-time physiological parametric information about patients. Such parametric information can include, among other things, a patient's heart rate or other heart function, blood pressure, blood oxygen level, and respiratory rate. This parametric information is typically detected by sensors, attached to a patient, and the sensors transmit the detected physiological information over a wired or wireless link to a patient monitoring device (either proximate to a patient or remote to the patient) which can in turn be in communication with a local network maintained by the healthcare organization. Subsequent to collecting patient parametric information, a monitor can analyze the information for the purpose of generating a message that includes information that causes and alarm to be generated and send to one or more appropriate clinicians alerting them to a patient's condition or event, which can be for example a low heart rate or low blood pressure condition. In order for a monitor to determine whether or not an alarm should be generated, a threshold value associated with each physiological parameter can be set. For example, if it is clinically determined that an alarm should be generated when a patient heart rate falls below eighty beats per minute, then the threshold value for recognizing a low heart rate can be set to eighty.

In a typical healthcare setting, one or more clinicians can be responsible for attending to multiple patients during a specified period of time (i.e., work shift). Depending upon the type of clinical unit (i.e., ER, ICU, etc.) in which a clinician is working, greater or fewer numbers of alerts can be generated and sent to them during their shift of work. In certain cases, if the number of alerts generated and sent to any one or more clinicians exceeds their ability to respond to the alerts with care for patients, and depending upon the type of alert they receive (ranging from critical type alerts to non-critical type alerts . . . i.e., respiratory arrest or need a bed pan), the clinician(s) may become desensitized to the alerts, and consciously or unconsciously ignore the alerts until they finish with a current task, if ever. This conscious or unconscious behavior to ignore alerts in the face of a large number of alerts is typically referred to as alarm fatigue, and alarm fatigue is a major cause of poor patient outcomes or mortality in clinical settings.

If one or more alerts are generated in response to clinical events that are not life threatening, such as a slightly elevated respiratory or heart rate for example, a workers behavior to temporarily or permanently ignore this type of alert will, in all probability not harm a patient. However, if as described above, due to receiving an overwhelming number of alerts during a shift (some of which can be critical and some of which may not be critical), the healthcare worker consciously or unconsciously ignores an alert that is generated as the result of a critical patient event, then the patient outcome may be at risk.

BRIEF DESCRIPTION OF THE DRAWINGS

The present invention can be best understood by reading the specification with reference to the following figures, in which:

FIGS. 5A and 5B represents a flow diagram of logic 400 that runs in the fatigue detection module 230 to detect clinician fatigue.

FIG. 6 is a flow diagram representing an optional embodiment of the logic 400.

TERMS

Figure 1:
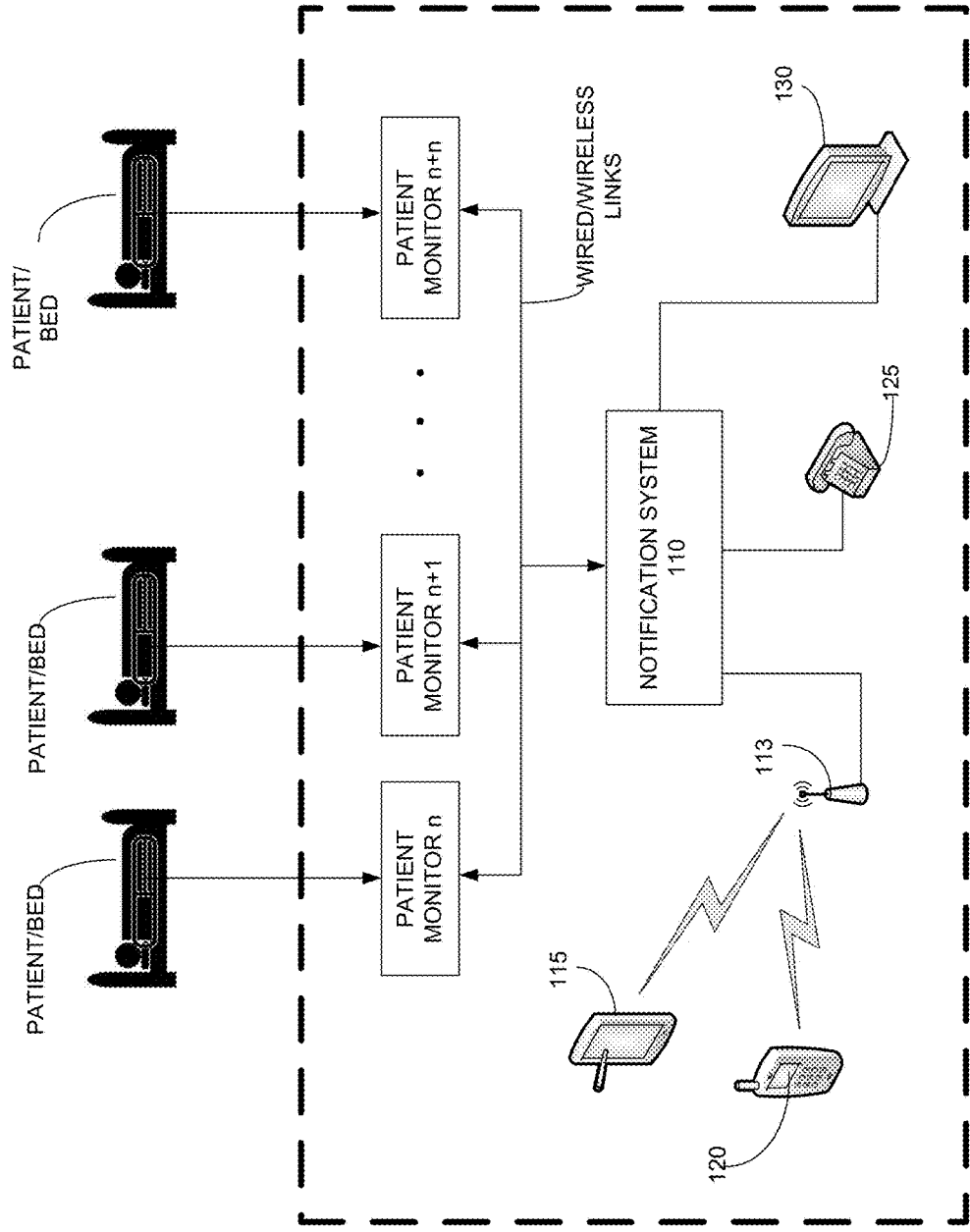
FIG. 1 illustrates a healthcare network 100 operating to detect and report clinical events generated by patient monitors.

An Alarm Message Instance is a single alarm received by the notification system that is associated with a particular patient bed.

Clinician Alarm Fatigue is the desensitization of a clinician to alarms received from the notification system.

An Event Notification System operates to receive event information from call points and information from clinicians and uses this information to detect alarm fatigue prior to, or at the time of, a clinician becoming desensitized to alarms.

An Alarm Fatigue Alert Message is an alert message generated by the alarm fatigue detection system when the number or value of alarms detected for any one or more beds during an alarm fatigue period becomes greater than the Average Alarm Fatigue Value by at least an Alarm Fatigue Alert Generation Threshold value.

An Alarm Fatigue Value is a numerical value assigned to a particular alarm type that corresponds to an amount of time needed by a clinician to care for a patient associated with the alarm.

Current Alarm Message Count or Value is a current numerical count or current fatigue value of all event messages received by the notification system from a particular call point.

Total Current alarm message count or Value is the sum of the current bed alarm message counts or fatigue values for all patient beds in an alarm fatigue area during an alarm fatigue period.

A Current Average Alarm message count or Value is the quotient resulting from dividing the Total Current alarm fatigue count by the number of beds in an alarm fatigue area.

An Alarm Fatigue Alert Message Generation Threshold represents a value (integer or percent) by which a Current Bed Alarm Message Count or Value exceeds a Current Average Alarm Fatigue Value to cause the Alarm Fatigue Detection System to generate a Clinician Alarm Fatigue Alert Message. The notification system can be configured with the threshold value, and the value can be specified to be a value that is greater than Zero.

The Alarm Fatigue area is an area that is comprised of some number (a set) of individual patient beds that are selected to be monitored as a group during a specified period of time. This area can represent the patients/beds assigned to one or more clinicians during a period of time.

The Alarm Fatigue Period is a selected/specified period of time during which the alarm fatigue detection system collects and maintains information used to recognize alarm fatigue. The alarm fatigue detection system can be configured with a rolling time period (of a specified duration) during which it collects and maintains information used to recognize alarm fatigue.

An Alarm Type is a unique identity that corresponds to each different type of clinical event detected by a patient monitor. An event type can be, but is not limited to, a heart rate low event, a heart rate high event, a blood oxygen level low event, a respiratory failure event.

DETAILED DESCRIPTION

A number of actions can be taken to mitigate the prevalence of alarm fatigue in the healthcare workplace. One technique that is employed to resolve the problem is to adjust monitor threshold values so that the monitor detects fewer events. For instance, low heart rate threshold can be set to a lower value (75 instead of 80 bpm for instance) such that an event is only detected if a patient's heart rate falls below seventy five beats per minute. Another technique that is used to prevent nuisance alarms is to suspend alarms that are generated due to short duration events. That is, if an event is active for less than a specified period of time (suspend time period), the monitor can cancel the event and not generate an alarm. Yet another solution to this problem is to tie the generation of an alarm to multiple different types of events (heart rate and blood pressure for instance). So, if a patient's heart rate is detected to fall below a threshold value (even for a short period of time) and at substantially the same time their blood pressure also falls below a threshold value, then the monitor can generate and send an alarm. It was found that making the generation of an alarm contingent on two related, but different types of events occurring at substantially the same time reduces the number of nuisance alarms generated by a monitor. Yet another method employed by healthcare organizations to mitigate alarm fatigue is to provide a comprehensive clinical alarm training program. Such a program can, among other things, educate workers to appropriate monitor settings, when alarms can be disabled, when monitor parameters can be altered, guidelines for who can and who may not alter parameters.

Despite the efforts to mitigate the problem of clinician alarm fatigue described above, alarm fatigue is still a major contributing factor to poor patient outcomes in healthcare and in other emergency response environments. Therefore, it would be advantageous if information generated by a patient, a patient monitor or by a clinician, and which is received by an event notification system, could be used to determine that a clinician responsible for a particular grouping of patient beds is either at risk of suffering from alarm fatigue at some point in the future, or is currently suffering from alarm fatigue.

Accordingly, I have invented methodology implemented in alarm fatigue detection functionality comprising an event notification system (ENS) that operates to detect clinician alarm fatigue either at the time a clinician begins to suffer from fatigue, or that operates to determine that a clinician may be at risk of suffering from alarm fatigue at some future time (i.e., before alarm fatigue effects a clinicians behavior/performance). According to a first embodiment, the ENS can operate on information it receives that relates to clinician activity to determine that alarm fatigue has occurred, and according to a second embodiment, the ENS can operate on information it receives in alarms that are unrelated to clinician activity to determine that a clinician may be at risk of suffering from alarm fatigue at some future time.

According to the first embodiment, the ENS can be configured so that it operates to receive information that is indicative of different types of clinician activity. This activity can be comprised of but is not limited to, (1) information that is indicative of a clinicians location and movement subsequent to a time that an alarm message is generated and prior to a time that an alert message that is generated by the ENS is responded to, (2) information that is indicative of a clinicians physical and/or emotional health (in poor physical health or are exposed to a stressful situation or sleep deprived), (3) information relating to a clinicians interaction with a patient or a patient monitor, (4) information relating to a clinicians response to alerts, relating to alerts that are escalated, or (5) information relating to any interaction the clinician has with the ENS (i.e., call point interaction). If the ENS detects any combination of two or more types of the information indicative of clinician activity, and depending upon metrics or characteristics that are assigned to the activity and threshold values that are specified for each activity, the ENS can determine that the clinician is currently suffering from alarm fatigue. An active clinical event according to this description is an event that is in progress.

According to the second embodiment, the ENS can be configured to receive, track the number of (or value of), and identify the origin of information it receives in alarms or event messages during a specified alarm fatigue period for an alarm fatigue area that is not related to clinician activity, and then use this information to determine that a clinician can be at risk of alarm fatigue at some future time. From one perspective, the ENS (notification system) can anticipate the onset of clinician alarm fatigue, and then generate and send an alarm fatigue alert message to someone other than the clinician who is at risk of alarm fatigue. The notification system can determine that a clinician is at risk of alarm fatigue in the future by calculating a current average alarm fatigue count by dividing a total current alarm fatigue count by the number of beds in an alarm fatigue area. If a current bed alarm message count for a bed is detected to be greater than the total current average alarm fatigue count by at least a specified alarm fatigue alert message generation threshold value, then the system can generate and send an alarm fatigue alert message to an appropriate individual other than the clinician who is at risk of alarm fatigue. The alarm fatigue alert message can have instructions, or suggestions that an individual, which may or may not be the clinician at risk of alarm fatigue, can act upon to prevent the clinician at risk from succumbing to alarm fatigue. Further, since some alarms may require more time to resolve than others, the notification system can be configured to distinguish between different types of alarms, and depending upon the type of alarm received, an alarm fatigue value can be assigned to an alarm type.

The alarm fatigue value can be different for some or all alarm types and is assigned by a system administrator. For example, the alarm fatigue value can be one for an alarm type that takes a clinician an average amount of time to resolve, it can be greater than one if the alarm type takes longer than an average amount of time to resolve, or the value can be less than one if the alarm takes less than the average amount of time to resolve. The amount of time that it takes a clinician to resolve each particular type of alarm can be determined empirically, and the alarm fatigue values can be stored in a lookup table in association with each different type of alarm.

The alarm fatigue alert message can be sent to an appropriate individual which may or may not be at future risk of alarm fatigue, and the message can have information that the individual can use to initiate corrective action, such as, and among other things, assigning more caregivers to an area, reassigning patients from the caregiver at future risk of alarm fatigue to another caregiver, instructing the caregiver at risk of future alarm fatigue to go on break. These and other advances in the area of alarm fatigue prediction are implemented in an ENS, hereinafter referred to as the notification system 110, which is connected to a healthcare network 100 and described below with reference to the figures.

The healthcare network 100, illustrated in FIG. 1, is comprised of devices that are configured to, among other things, receive patient related (clinical) information, and based upon the type of clinical information received, determine whether or not to report and/or how to alert the appropriate healthcare staff to the clinical information. The network 100 is, in this case, comprised of a plurality of patient monitoring devices, the notification system 110, and a plurality of different types of mobile or fixed network communication devices 115, 120, 125 and 130 which are in communication with the notification system 110 over either wired or wireless mediums. Each patient monitor can receive information from one or more sensors that operate to detect physiological or clinical information relating to a patient. As described earlier, this clinical information can include, but is not limited to heart rate, blood pressure, respiratory rate, blood oxygen, body temperature, and other information. Clinical information detected at each sensor is transmitted to a patient monitor that generally operates to identify clinical events that can be reported to the appropriate member(s) of a clinical staff. Typically, a patient monitor is configured to determine whether an event is clinically significant and should be reported, and if so, sends an alarm to the notification system 110. As mentioned above, the notification system 110, is shown in FIG. 1 to be connected to the healthcare network 100, and it generally operates to, among other things, receive information generated as the result of a clinician activity, or to receive information that is generated by activity unrelated to a clinician. The patient clinical information comprises any information that can be detected by a patient monitor and sent to the system 110, and the information generated as a result of clinician activity can be information generated by a clinician in a response to an alert message, or can be any information that a clinician enters in the system 110, which can be comprised of but is not limited to, (1) information that is indicative of a clinicians location and movement during the time an alarm is active, (2) information that is indicative of a clinicians physical and/or psychological health (in poor physical health or are exposed to a stressful situation), (3) information relating to a clinicians interaction with a patient or the patients monitor, (4) information relating to a clinicians responses to alerts, relating to alerts that are escalated, or (5) information relating to any interaction the clinician has with the notification system.

Functionality comprising the notification system 110 will now be described with reference to FIG. 2. In the description that follows, the terms alarm messages and event messages may be used interchangeably, and for the purpose of this description, both terms are synonymous. The notification system 110 functionality can be implemented in any suitable network computer/server device that is configured to operate in a clinical setting, such as in the healthcare network 100 of FIG. 1. Generally, the notification system has specially designed functionality that operates to receive event information in the form of alarm messages, and to receive responses from clinicians to alert messages generated by the notification system as the result of the alarm messages. The alarm messages are generated by a variety of different types of call points, and clinician responses to alert messages are typically received by the notification system from mobile or stationary communication devices under the control of the clinician. The notification system uses event information comprising an alarm message to determine what type of alarm is received, to determine the source of the alarm, to maintain a count of each alarm that is received, and the notification system maintains a store of the event information comprising each alarm. The event information comprising each alarm can be maintained in a database designed to have a plurality of separate records for maintaining event information in alarm messages received from each all point in each alarm fatigue area (i.e., clinical unit such as an ER, OR, etc. This event information can be used by the notification system to determine whether to generate and send an alert message, and to determine what type of an alert message should be generated, and according to one embodiment, some or all of this information can be used to determine whether a clinician may suffer from alarm fatigue at some future time. The alerts can be sent to a wireless communication device (such as the tablet device 115 and/or the smart phone 120), and/or the alert can also be sent to a wired communication device such as the phone 125 or the nurse call station 130, all of which devices are shown with reference to FIG. 1.

As described above, the notification system 110, can also receive information generated as the result of clinician related activity, such as a clinician response to alert messages, or information entered into the system by the clinician (i.e., state of physical health of the clinician, whether a clinician is currently attending to a patient, the timeliness of a clinicians response to alerts, statistics relating to alert message sent to a particular clinician that are escalated, a clinicians movement and current location, and any other interaction a clinician may have with the notification system). According to another embodiment, this clinician related activity information can be used by the notification system 110 to determine whether or not the clinician is currently suffering from alarm fatigue.

The notification system 110 described above and illustrated with reference to FIG. 2 has a number of different functional modules. Among other things, it has an event message processor module 200, it has an alert message generation and response module 210, and it has a fatigue detection module 230. The event message processor module 200 generally operates to receive information associated with events generated by call points such as, but not limited to, any one of the patient monitors described with reference to FIG. 1. The alert message generation and response module 210 generally operates to receive the information associated with clinician activity (alert message responses from clinicians and other clinician input to the ENS) and to process this information to determine if other messages should be generated, and the fatigue detection module 230 generally operates on information maintained in the event message processor 200 and the alert message generation and response module 210 to detect that a clinician is current suffering from, or may at some point in the future suffer from, alarm fatigue.

Figure 2:
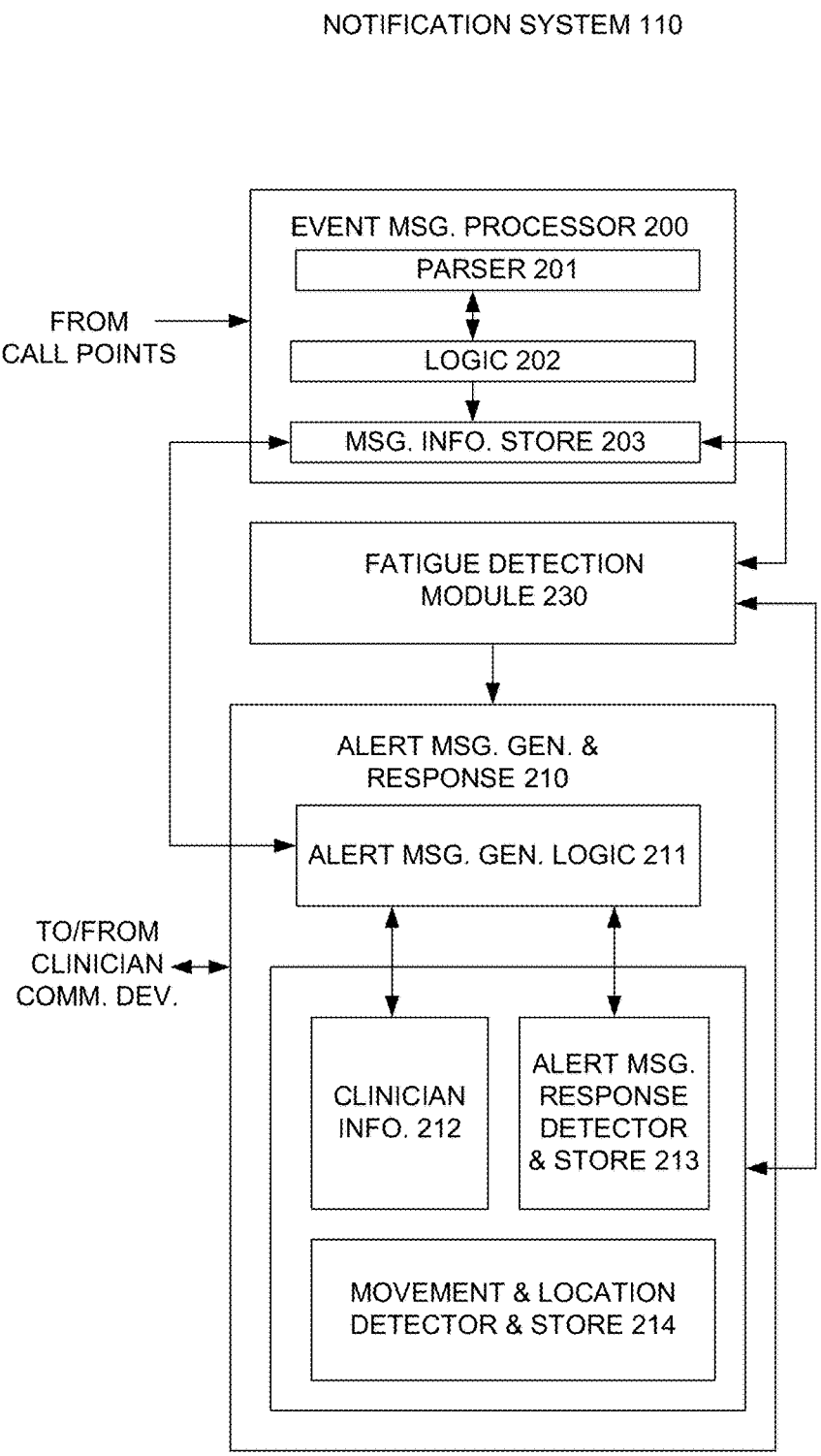
FIG. 2 shows functional elements comprising a notification system 110 comprising the network in FIG. 1.

More specifically with reference to the event message processor module 200 in FIG. 2, this module has a parser 201 that is designed to identify, among other things, particular types of information comprising an event message, such as the source (call point ID) of an event message, the time the event message is generated, clinical information in the event message, the clinical unit (i.e., fatigue area) in which the call point is located, a bed number and patient name. The ENS can cause the parsed event message information to be temporarily stored in computer memory, or other storage device (not shown) associated with it, where the logic 202 (associated with the database) can operate on the information to increment an event/alarm message count maintained in a message information store 203, and to determine a type of the received event message which can also be maintained in the store 203. The parsed information that is operated on by the logic 202 can be stored in a database record corresponding to the identity of a call point (or bed) located in an alarm fatigue area. According to this description, a database record relating to each call point is referred to as a virtual call point (VCP), and the structure of an example VCP will be described later with reference to FIG. 3A.

Continuing to refer to FIG. 2, and as described earlier, the alert message generator and response module 210 is generally designed to operate on event message information maintained in the store 203, and to receive information indicative of different types of activities engaged in by a clinician in the course of performing their duties, and to use this information to determine whether to generate a particular type of alert message that is sent to a clinician. The module 210 is comprised of logic 211, a clinician information module 212 that operates to receive information entered into the notification system by a clinician (other than alert response information), an alert message response detector and store 213, and it is comprised of a clinician movement and location detector and store 214. The clinician information 212 can be stored in one or more files (not shown) accessible by the logic 211 that operates to generate alert messages and to receive alert response message. The clinician information 212 can be, among other things, information relating to one or more instances of an interaction the clinician has with a patient, information relating to a clinician location and/or movement, and information entered into the notification system by the clinician relating to the state of the clinician's physical or mental health. The clinician information module 212 can also have functionality that prompts a clinician for information, such as how much sleep did you get prior to starting work, or the state of their physical or emotional health, and this information can be stored for use by the fatigue detection module 230. The alert message response detector and store 213 operates to detect messages generated by a clinician in response to an alert or to escalation messages, and to parse and store information in the response messages, such as the time a response is received, the identity of an alert message to which a clinician is responding, or any other information. Further, the alert message response detector 213 would have functionality that can maintain a current average response time or metric (time from sending alert message to receiving a response from a clinician) for all of the responses received by a clinician during a response period. The information stored in 213 is accessible by the logic running in the fatigue detection module 230 to determine whether a clinician is currently suffering from alarm fatigue. The movement and location detector and store 214 can operate to receive current position and movement information from a mobile communication device and store this information where it can also be operated on by the logic running in the fatigue detection module 230. The position information can be the identity of a beacon in a known location or it can be geographic positioning system information, and the movement information can be generated by an accelerometer operating on a mobile communication device controlled by the clinician.

Figure 3A:
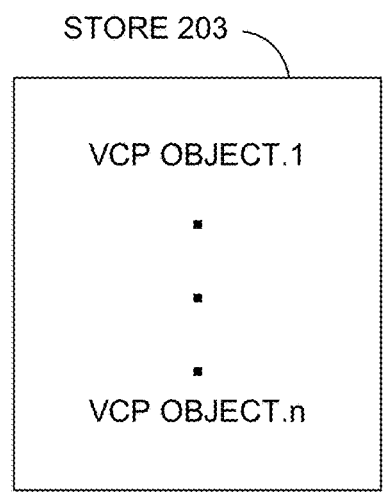
FIG. 3A shows a store 203 of virtual call point (VCP) Objects.

Referring now to FIG. 3A, a store 203 of a plurality of instances of virtual call point (VCP) objects, VCP object.1 to VCP object.n, comprises the store 203 maintained in the event message processor 200. Each instance of a VCP object is typically dedicated to storing event information in event messages that have been received from one call point, but a VCP object can be designed to receive event information from more than one call point (i.e., more than one patient monitor). The VCP object can maintain information relating to each of a plurality of event messages separately, where it can be accessed as needed by the fatigue detection module 230 to determine that a clinician may be at risk of alarm fatigue at some future time, and by logic comprising the alert generation and response module 210. Event information comprising a VCP object, the object.n in this case, is shown and described with reference to FIG. 3B.

Figure 3B:
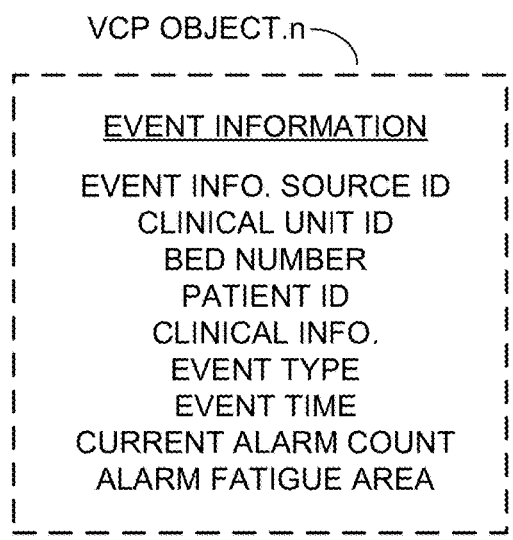
FIG. 3B shows event information comprising a VCP Object.

The VCP object.n in FIG. 3B is comprised of the identity of the call point (i.e., patient monitor(s)) that sent the event information to the notification system 110, the identity of a clinical unit in which the call point is located (i.e., ER1), information identifying a patient bed or a patient with which the call point is associated, information indicative of the time an instance of an event (i.e., event message) is detected, a current count of the number of event messages/alarms that have been received from the call point during the current alarm fatigue period, and the identity of the alarm fatigue area associated with the call point to which the VCP object.n is related. For the purpose of this description, a physical call point can be comprised of a single patient monitor, or it can be comprised of several monitors associated with a single patient occupying a single hospital bed.

The alarm fatigue detection module 230, briefly described earlier with reference to FIG. 2, has a number of functional elements that operate on information comprising the VCP objects in the store 203, and on information maintained in the alert message generator and response module 210 to, as described earlier, determine whether a clinician is currently suffering from alarm fatigue, or is at risk of suffering from alarm fatigue at some future time. More specifically with reference to FIG. 4A, the alarm fatigue detection module 230 has logic 400 that operates on information comprising the VCP objects in the store 203, that operates on information stored in association with the alert message generation and response module 210, and it operates on certain fatigue values stored locally to determine whether a clinician may be currently suffering from alarm fatigue, or is at risk of suffering from alarm fatigue in the future.

Figure 4A:
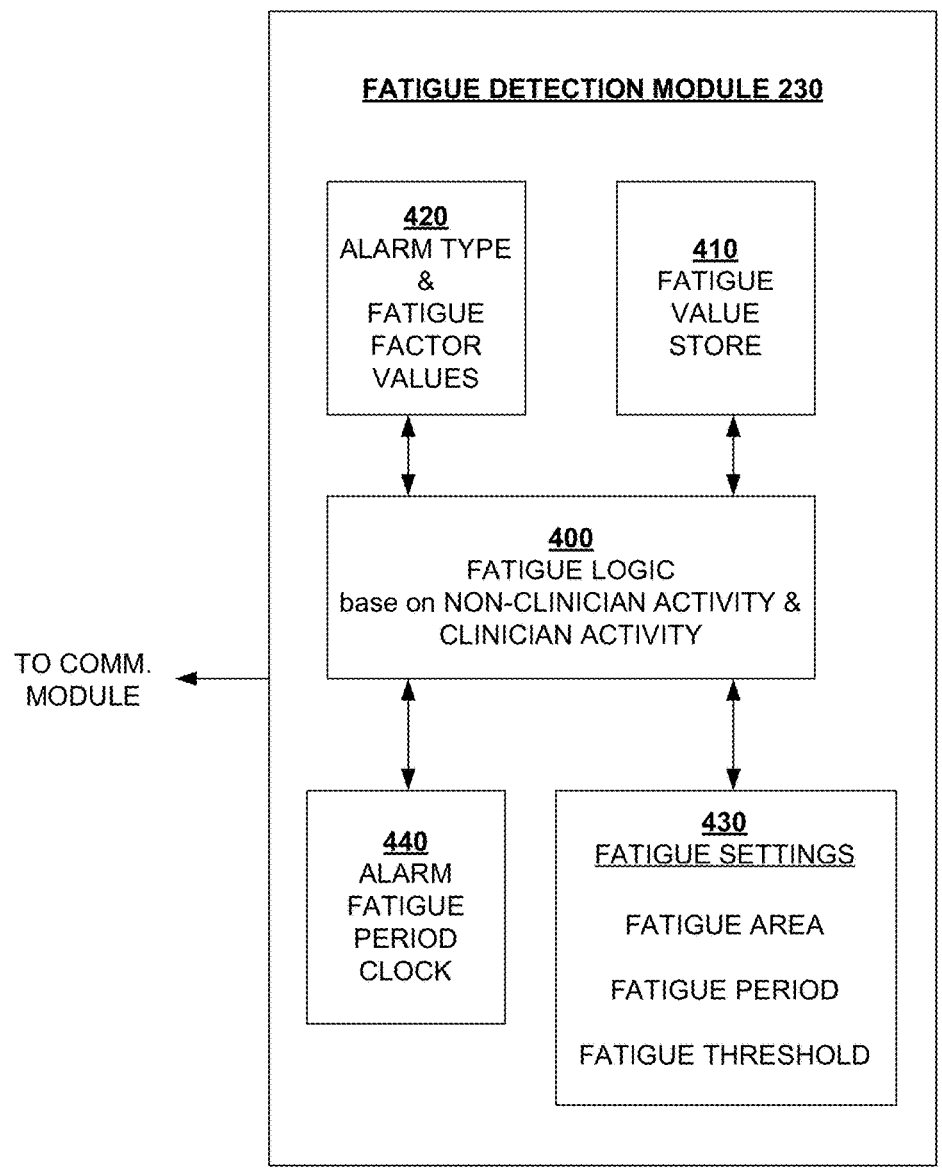
FIG. 4A is a block diagram showing functionality comprising a fatigue detection module 230 comprising the notification system 110.

Continuing to refer to FIG. 4A, the fatigue detection module 230 maintains, among other things, a listing 420 that associates alarm message types with fatigue values. An exemplary format for this listing is shown with reference to FIG. 4C. Each type of event or alarm can be assigned a fatigue value that can correspond to some empirical or quantitative measure of a clinician's response to each type of event. The measure can be the average time it takes a clinician to resolve a particular type of event, or the number of clinicians it typically takes to resolve the event for example. As previously described, the fatigue values can be assigned to each type of event message by an administrator. The fatigue detection module also maintains settings 430 that relate to the identity of beds or call points comprising a fatigue area, that relates to fatigue period starting and stopping times, and that relates to a fatigue threshold value. Patient beds, or associated call points, that are the responsibility of a single clinician are typically assigned to one fatigue area, or group of patient beds can be assigned to more than one fatigue area depending upon a patient's particular care needs. The fatigue period is typically set to be of a particular number of hours associated with a work shift, and the fatigue period hours can be tracked on a rolling basis (i.e., an 8 or 12 hour period having a start and stop time that changes with the time of the day), or that is static (i.e., starts at a set time and ends at a set time). For the purpose of determining clinician fatigue, the logic 400 only uses information received by the notification system 110 having time stamp information that falls within the starting and stopping times of the current fatigue period. The fatigue threshold value described above can be an integer value, a fractional value, or it can have an integer value component and a fractional value component, and this value is used by the logic 400 to determine which patient bed or beds many be the source of clinician alarm fatigue. This threshold value can be determined empirically.

Figure 4B:
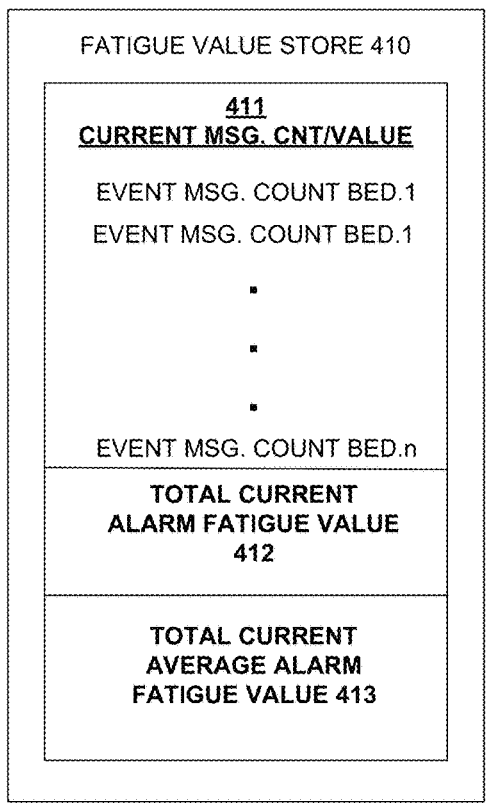
FIG. 4B is a diagram showing different information maintained by the notification system 110 in a fatigue value store 410 comprising the fatigue detection module 230.
Figure 4C:
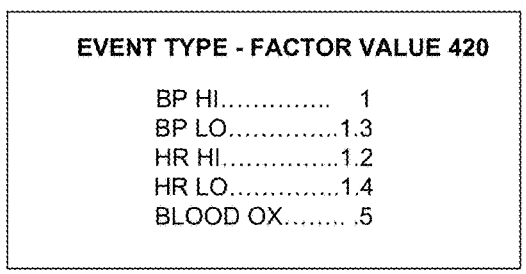
FIG. 4C is a listing of event message types and their assigned fatigue values.

The fatigue detection module 230 also has a store 410 of alarm fatigue values calculated by the logic 400 and it has listing or record 420 that associates an event type with a fatigue value. As each value is calculated by the logic, it is added to a current bed alarm message count or value also maintained in the store 410 in association with a particular patient bed, and shown with reference to FIG. 4B. FIG. 4B shows the fatigue value store 410 maintaining a listing 411 of current message counts or values 411 for each patient bed comprising a fatigue area, maintaining a total current alarm fatigue count or value 412 for a fatigue area which is the sum of the counts of values maintained in 411, and the store 410 maintains a total current average alarm fatigue value 413 that, as described earlier, represents a quotient arrived at by dividing the total current alarm fatigue count 412 by the total number of beds in the fatigue area. The listing 420 is accessed by the fatigue logic 400 in order to calculate a current event message value.

The operation of the fatigue logic 400 to determine whether a clinician is currently suffering from alarm fatigue, or is at risk of suffering from alarm fatigue at some future time, will now be described with reference to FIGS. 5A, 5B and 6. While the logic 400 is described to operate exclusively on either information generated by a clinician or information not generated by a clinician in order to determine whether a clinician is currently suffering from alarm fatigue, or is at risk of suffering from alarm fatigue, this does not necessarily have to be the case. For example, information comprising certain activities a clinician engages in with the notification system could be used to predict alarm fatigue. A clinician response to an alert message is one such activity. According to this embodiment, the fatigue detection module can identify that a clinician's responses to some number of past alert messages within some predetermined period of time is taking increasing more time. When the module 230 detects such a trend for the predetermined period of time, it can cause a message to be sent to the alert generation module 210 with instructions to send an alert message to an individual other than the clinician at risk of alarm fatigue.

Referring now to the decision block 500 in FIG. 5A, the logic 400 continually operates to periodically detect new information sent to the notification system 110 from call points and from clinicians. When new information is received, the logic determines if the information is associated with an event message or is information entered into the system by a clinician. If the former is true, the logic proceeds to block 501 and determines the source of the event message and to determine which of one or more clinician is currently responsible for the patient bed that is the source of the event message, otherwise the logic examines the information to determine whether it is entered into the system by a clinician. A listing of clinicians to patient bed assignments (not shown) can be maintained by the notification system 110. After determining the event message source in block 501, the logic proceeds, in block 502, to increment an alarm message count (411) for the patient bed associated with the source of the event messages and to update the total alarm count for the fatigue area to be current and to store these values in the store 410. As described earlier, this current alarm fatigue count is the sum of the event message counts for all patient beds in a fatigue area. In block 503, the logic proceeds to calculate a current average alarm fatigue count and to store this count in the store 410. In the decision block 504, the logic 400 operates to examine the event message counts for each patient bed in the fatigue area looking for any bed with a count that is greater than the total current average alarm fatigue value by an amount that is equal to or greater than a specified alarm fatigue alert message generation threshold value. If the logic determines that the current alarm count for one or more beds is greater than the average alarm fatigue count by an amount that is equal to or greater than the threshold, then it sends a message to the alert message generator 210 with instructions to send an alert message to an individual, who may or may not be the clinician responsible for the beds identified in block 504, indicating that the clinician responsible for these beds is at risk of suffering from alarm fatigue at some future time.

Figure 5B:
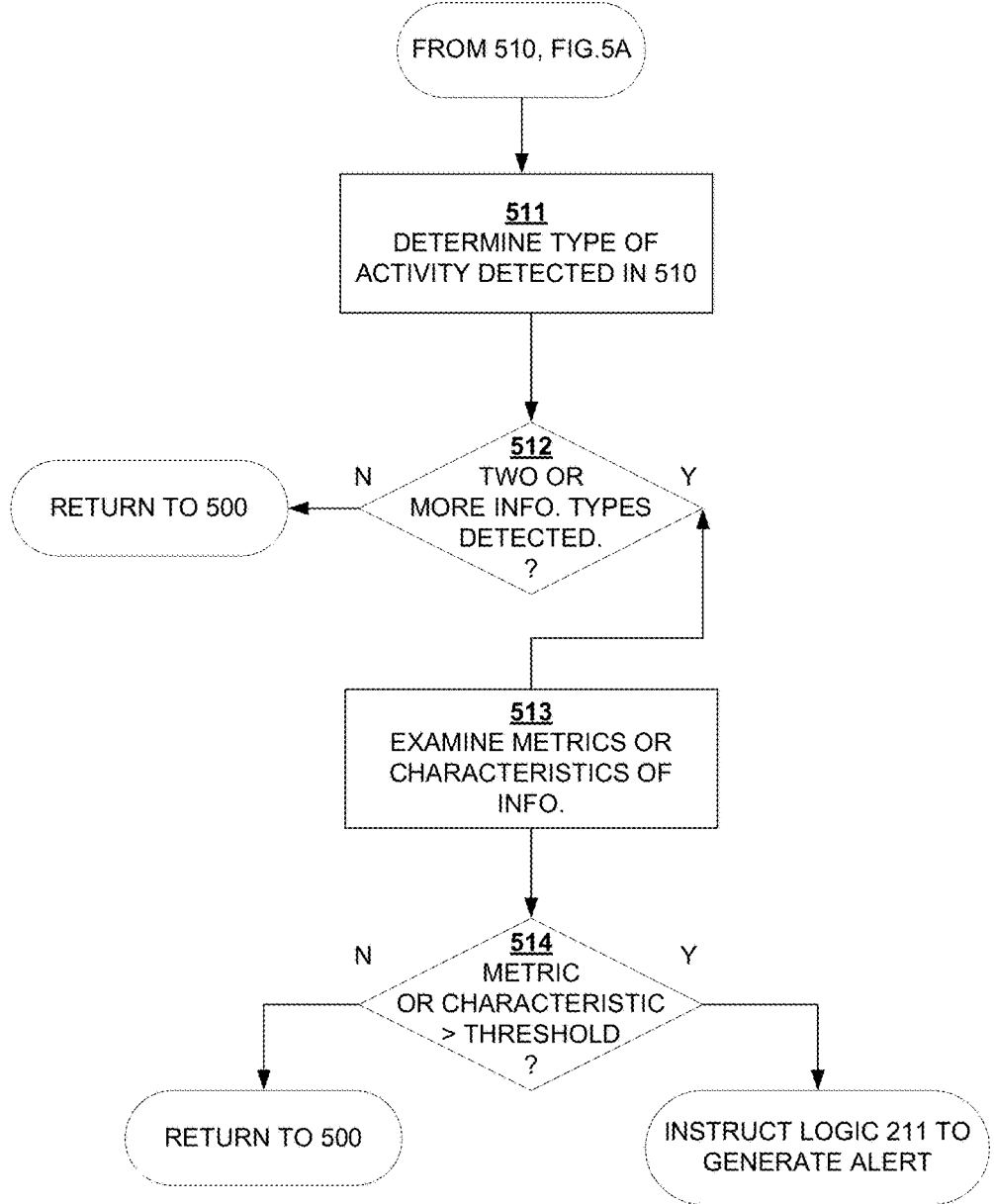

Continuing to refer to FIG. 5A, if at the decision block 500 the logic 400 determines that the new information received by the notification system 110 is not related to an event message, then the process proceeds to the decision block 510 and the logic examines the new information to determine whether it was entered into the system by a clinician (i.e. an alert response message, information indicative of clinician health, information indicative of a clinician's current location and movement, etc.). If, in block 510, the logic determines that a clinician has entered the new information into the system, then the process proceeds to the decision block 511 that is shown in FIG. 5B. In block 511 the logic identifies the type of activity the clinician (or the clinician communication device) engages in with the notification system and stores an indication of the activity type and other information associated with the activity in the appropriate stores comprising the alert message generation and response module 210. For example, the type of activity can be a clinician responding to an alert or escalation message, or a clinician entering their health information into the system, or information indicative of a current clinician location and/or movement or their interaction with a patient monitor. Then, in the decision block 512 the logic can examine all of the stores (212, 213, and 214) for current information indicative of instances of clinician activity (i.e., alert message response, interaction with a patient monitor, current clinician health, movement and location information, etc.), and if the logic detects that two or more different types of clinician activity instances are stored, then the logical process proceeds to block 513, where the logic examines information comprising the two or more instances of activity in order to identify metrics or characteristics that it can used in determining whether a clinician is currently suffering from alarm fatigue. Then, in the decision block 314, the logic determines whether any of the metrics identified in block 513 exceeds a fatigue threshold value, and if one or more metrics do exceed the threshold value, then the fatigue detection module 230 can send a message to the alert message generation module 210 that includes instructions to generate and send an alert message to one or more clinicians, that may or may not be suffering from fatigue, that alerts them to the clinician who is suffering from alarm fatigue.

The fatigue threshold value in the decision block 514 can, for example, represent a period of time from when an alert message is transmitted to a clinician to when the clinician responds to the alert message, this threshold value can be a period of time from receipt of an alert message to when a clinician to move away from their current location toward a location associated with an alert message, this value can a number of hours of sleep during prior to working a shift, or this value can be associated with a clinician health metric. This threshold value, which is different than the alarm fatigue alert message generation threshold referred to in the decision block 504 in FIG. 5A, can be determined based upon empirical evidence gathered over time in a clinical environment. As described above, the ENS can calculate or assign a metric value each of the different type of clinician activities. For example, a particular value can be assigned to the health of a clinician if they report that they are suffering from a cold or the flu. A different value can be assigned if the clinician indicates that they are suffering from sleep deprivation, or if there has been a death in their family, etc.

According to the embodiment described with reference to FIG. 5A, the logic 400 operates to maintain a count of the number of alarm messages the notification system receives during a fatigue period, and uses this count to determine whether a clinician may be at risk of suffering from alarm fatigue at some future time. An alternative embodiment to the logic 400 described in FIG. 5A is now described with reference to FIG. 6. According to this alternative embodiment, the logic does not base an alarm fatigue determination on a count of the number of alarm messages received by the notification system 110, but rather bases a determination of alarm fatigue on an alarm fatigue message value. As described earlier, this alarm message value is the sum of the alarm fatigue values for all call points in an alarm fatigue area, and the alarm fatigue values for each alarm type can be determined according to empirical evidence gathered in a clinical setting. In the decision block 600 of FIG. 6, the logic 400 continually operates to periodically detect new information in event messages sent to the notification system 110 from call points. If the logic detects new event message information, the process proceeds to block 601 at which point the logic determines the source of the event message, determines the type of information comprising the event message (the message type identified can be BP LO for example), and identifies one or more clinicians assigned to the patient bed that is the source of the event message. A clinician to patient bed assignment listing (not shown) can be maintained by the notification system. Then, in block 602 the logic 400 uses the event message type (BP LO) identified in block 601 to lookup (in the listing in FIG. 4C) a fatigue value associated with the event message type, which in this case is the value 1.3. Then, after determining the alarm fatigue value for the event message instance, the current alarm message value for the patient bed associated with the event message is updated to be a new current alarm message value by adding the value of the alarm message determined in block 602 to the current alarm message value for the patient bed, and the total current alarm fatigue count (sum of all current alarm fatigue counts for each bed in the fatigue area maintained in the store 410) is updated.

Continuing to refer to FIG. 6, in block 603 the logic 400 calculates a current average alarm fatigue value by dividing the total current alarm fatigue count by the number of patient beds in the alarm fatigue area, and this value is maintained in the store 410. The logic 400 periodically examines the current alarm message values associated with each patient bed in the fatigue area, and if in the decision block 604 the logic determines that the current alarm message value for any one or more patient beds exceeds the total current average alarm fatigue value by a threshold value, then the logic sends a message to the alert message generation module 210 that includes instructions that cause the module 210 to generate and send an alarm fatigue alert message to one or more clinicians who are or are not the clinicians at future risk of alarm fatigue. While the ENS will typically sent the alarm fatigue alert message only to a clinician that is not currently experiencing alarm fatigue, it may be the case that the clinician currently experiencing alarm fatigue also receives a similar alarm fatigue alert message from the ENS. In this case, the alarm fatigue alert message can include instructions to check on the proper operation of a patient monitor, or the message may question information the clinician has entered into the system.

While the alarm fatigue detection methodology is described here in the context of a healthcare setting, this does not necessarily have to be the context in which this methodology is implemented. For example, the alarm fatigue detection methodology can be implemented in a public safety 911 system environment (for police calls or fire alarms). In such an environment, event messages can be generated automatically by a security system or a fire or smoke detection system (both of which are considered to be considered as call points) and sent to a 911 emergency management system (event notification system) that is being monitored by a 911 operator, or event messages can be generated by individuals (i.e., a call point) who call a 911 emergency management system.

The forgoing description, for purposes of explanation, used specific nomenclature to provide a thorough understanding of the invention. However, it will be apparent to one skilled in the art that specific details are not required in order to practice the invention. Thus, the forgoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

I claim:

1. A method for detecting alarm fatigue, comprising:
   receiving and maintaining, by an event notification system, information that is indicative of at least two different types of an activity performed by a first clinician in an alarm fatigue area during an alarm fatigue period;
   using the activity information to determine a metric value that is assigned to each one of the at least two different types of clinician activities;
   determining that a current value of the metric assigned to one of the at least two clinician activities is equal to or greater than a fatigue threshold value corresponding to the at least one clinician activity; and
   generating and sending an alarm fatigue alert message to a first or to a second clinician indicating that the first clinician is currently suffering from clinical alarm fatigue.

2. The method of claim 1, wherein the at least two different types of first clinician activities are comprised of any combination of information relating to a time at which the first clinician starts moving from a current location subsequent to a time at which an alert message is received, information that is indicative of the first clinicians physical or emotional health, information relating to the first clinician interactions with a patient or patient monitor, information relating to a plurality of instances of the first clinician responses to alert messages, and information relating to an interaction the first clinician has with the event notification system.

3. The method of claim 2, wherein the metric assigned to each instance of the activity associated with the first clinician responses to alert messages has a value that is equivalent to a duration from a first time at which the alert message is sent and a second time at which the first clinician responds to the alert message, and this metric value is maintained for each of one or more of the activity instances.

4. The method of claim 3, wherein a current average value for the metrics assigned to the first clinician activity instances associated with the first clinician responses is used to determine whether the first clinician activity is currently contributing to alarm fatigue.

5. The method of claim 4, wherein the current average value of the metric associated with the clinician responses to alert messages is a quotient equal to a sum of all the alert response period metrics divided by the number of responses to alert messages generated by the clinician.

6. The method of claim 1, wherein the first clinician is currently responsible for, and the second clinician is not currently responsible for, responding to an alert message generated by the event notification system in response to an alarm message received by the event notification system from one the plurality of the call points associated with the alarm fatigue area.

7. The method of claim 1, wherein the alarm fatigue area comprises a plurality of call points each one having a unique identity.

8. The method of claim 1, wherein the alarm fatigue period starts at a first time and ends at a second time.

9. The method of claim 8, wherein the alarm fatigue period is either a fixed period of time with specified beginning and ending times, or is a fixed period of time with a starting time that advances over time.

10. A system for detecting alarm fatigue, comprising:
    an event notification system, in communication over a network with call points which generate alarms in an alarm fatigue area and in communication with clinician communication devices, operating to receive information that is associated with a plurality of different types of activities performed by a first clinician in the alarm fatigue area during an alarm fatigue period and to determine values for metrics that are assigned to each of the plurality of the different activities, and the event notification system sending an alarm fatigue alert message to a first or a second clinician indicating that the first clinician is currently suffering from alarm fatigue if it is determined that the metric assigned to any one of the plurality of the different activities performed by the first clinician has a current value that is equal to or greater than a corresponding fatigue threshold value.

11. The system of claim 10, wherein the network is a wireless or a wired network.

12. The system of claim 10, wherein the plurality of different types of the first clinician activities are comprised of any combination of information relating to a time at which the first clinician starts moving from a current location subsequent to a time at which an alert message is received, information that is indicative of a clinicians physical or emotional health, information relating to the first clinician interactions with a patient or patient monitor, information relating to a plurality of instances of the first clinician responses to alert messages, and information relating to an interaction the first clinician has with the event notification system.

13. The system of claim 12, wherein the metric assigned to each instance of the activity associated with the first clinician responses to alert messages has a current value that is equivalent to a duration from a first time at which the alert message is sent and a second time at which the first clinician responds to the alert message, and this metric value is maintained for each of one or more of the activity instances.

14. The system of claim 13, wherein a current average value for the metrics assigned to the first clinician activity instances associated with the first clinician responses is used to determine whether the first clinician activity is currently contributing to alarm fatigue.

15. The system of claim 14, wherein the current average value of the metric associated with the clinician responses to alert messages is a quotient equal to a sum of all the alert response period metrics divided by the number of responses to alert messages generated by the clinician.

16. The system of claim 10, wherein the first individual is currently responsible for, and the second individual is not currently responsible for, responding to an alert message generated by the event notification system in response to an alarm message received by the event notification system from one the plurality of the call points associated with the alarm fatigue area.

17. The method of claim 10, wherein the alarm fatigue area comprises a plurality of call points each one having a unique identity.

18. The method of claim 10, wherein the alarm fatigue period starts at a first time and ends at a second time.

19. The method of claim 18, wherein the alarm fatigue period is either a fixed period of time with specified beginning and ending times, or is a fixed period of time with a starting time that advances over time.

* * * * *